(12) United States Patent
De Vos

(10) Patent No.: US 7,659,056 B1
(45) Date of Patent: Feb. 9, 2010

(54) METHOD AND APPARATUS FOR DETECTING A MUTATION IN A NUCLEIC ACID FRAGMENT IN A SAMPLE

(75) Inventor: Gerrit Johannis De Vos, Hendrikskinderen (NL)

(73) Assignee: Ingeny Holding B.V., Goes (NL)

( * ) Notice: Subject to any disclaimer, the term of this patent is extended or adjusted under 35 U.S.C. 154(b) by 776 days.

(21) Appl. No.: 10/399,826

(22) PCT Filed: Oct. 23, 2000

(86) PCT No.: PCT/NL00/00769

§ 371 (c)(1),
(2), (4) Date: Sep. 2, 2003

(87) PCT Pub. No.: WO02/38809

PCT Pub. Date: May 16, 2002

(51) Int. Cl.
*C12Q 1/68* (2006.01)
*C12P 19/34* (2006.01)
*C07H 21/04* (2006.01)

(52) U.S. Cl. ............... 435/6; 435/91.2; 536/23.1
(58) Field of Classification Search ............ 435/6, 435/91.2; 536/24.33
See application file for complete search history.

(56) References Cited

U.S. PATENT DOCUMENTS

| 5,451,500 | A |   | 9/1995 | Stapleton |   |
|---|---|---|---|---|---|
| 5,616,478 | A |   | 4/1997 | Chetverin et al. |   |
| 5,795,720 | A | * | 8/1998 | Henco et al. | 435/6 |
| 5,871,908 | A | * | 2/1999 | Henco et al. | 435/6 |
| 6,261,431 | B1 | * | 7/2001 | Mathies et al. | 204/601 |
| 6,492,118 | B1 | * | 12/2002 | Abrams et al. | 435/6 |
| 6,642,000 | B1 | * | 11/2003 | Strizhkov et al. | 435/6 |

FOREIGN PATENT DOCUMENTS

| EP |   | 0834729 A |   | 4/1998 |
|---|---|---|---|---|
| WO |   | WO 9102815 A |   | 3/1991 |
| WO |   | WO 9730346 A |   | 8/1997 |
| WO |   | WO 9730346 A1 | * | 8/1997 |

OTHER PUBLICATIONS

Zhang et al. On-line coupling of polymerase chain reaction and capillary electrophoresis for automatic DNA typing and HIV-1 diagnosis. J Chromatography B., vol. 714, p. 3-11, 1998.*

Zahang Nanyan et al: "On-line coupling of polymerase chain reaction and capillary electrophoresis for automatic DNA typing and HIV-1 diagnosis." Journal of Chromatography B, vol. 714, No. 1, Aug. 28, 1998, pp. 3-11.

Kenney Mary et al: "Mutation typing using electrophoresis and gel-immobilized acrydite probes." Biotechniques, vol. 25, No. 3, 1998, pp. 516-521.

* cited by examiner

*Primary Examiner*—Suryaprabha Chunduru
(74) *Attorney, Agent, or Firm*—Barbara E. Johnson, Esq.

(57) ABSTRACT

A method and apparatus for the detection of polymorphisms in a nucleic acid sample (e.g. blood, sperm, saliva, cells, . . . ). To enhance the efficiency and the reliability of the known methods (e.g. DGGE, SSCP and TGGE) the amplification process (e.g. PCR) preceding the actual detection step is performed in or on the polyacrylamide gel. Multiple gradients (of chemical denaturants, thermal denaturants and of porosity of the gel matrix) are used for the separation of DNA fragments, by zone electrophoresis on gel slabs or by capillary electrophoresis.

11 Claims, 5 Drawing Sheets

METHOD AND APPARATUS FOR DETECTING A MUTATION IN A NUCLEIC ACID FRAGMENT IN A SAMPLE

BACKGROUND OF THE INVENTION

1. Field of the Invention

The invention relates to a method and a device for detecting one or more mutation(s) in a nucleic acid fragment in a sample.

2. Brief Description of the Prior Art

Methods are known for screening nucleic acid fragments, in particular DNA fragments, for determined mutations. One method includes the following steps, to be performed in suitable sequence, of:

(a) amplifying the nucleic acid fragment present in the sample;

(b) separating the nucleic acid fragments by means of gel electrophoresis in the presence of a gradient resulting in at least partial melting of the double-stranded nucleic acid fragments formed in step (a), for the purpose of fixing the partially melted nucleic acid fragments at a specific location in the gel; and (c) detecting the separated nucleic acid fragments. It is known that mutations in the DNA can result in hereditary diseases and/or particular forms of cancer. Demonstrating such a mutation in the DNA in a sample of a patient can therefore be important in establishing whether the patient is a carrier of an abnormal gene responsible for a determined genetic disease, or in making a reliable diagnosis. DNA mutation research can also be important for instance in determining the risk of developing particular types of cancer, designing treatment in the case of tumours, in scientific research into links between diseases and particular genetic defects and in tissue typing.

In order to enable detection of a mutation in a nucleic acid fragment, such as for instance in the DNA, in a sample, the nucleic acid fragment present in the sample, which is usually present in the sample in too small a number of copies or as part of a larger nucleic acid fragment, must first be amplified to obtain sufficient material. Use is generally made for this purpose of conventional amplification techniques, such as for instance PCR. After the amplification step the amplified double-stranded DNA fragments must be separated from each other before they can be detected. For this purpose use is generally made of techniques based on gel electrophoresis. A drawback of the present method however is that both the amplification step and the separation step are time-consuming processes, whereby a great deal of time is required to perform the method. Since large numbers of samples often have to be screened, it is desirable that a method be developed with which a large number of samples can be examined in rapid and simple manner for the presence of one or more mutations in the nucleic acid fragments present in the sample.

SUMMARY OF THE INVENTION

The invention therefore has for its object to provide a method for detecting one or more mutation(s) in a nucleic acid fragment in a sample, wherein a large number of samples can be examined in a short time for the presence or absence of a mutation.

This object is achieved by the invention in that according to the invention the amplification step is performed in or on the gel.

By carrying out the amplification step in or on the gel the method can be performed in a shorter time. Immediately subsequent to the amplification step the amplified nucleic acid fragments are herein separated from each other by applying a voltage over the gel after the amplification, whereby the electrophoresis is started. It is therefore no longer necessary after performing the amplification step to place the sample onto the gel for the subsequent electrophoresis step. During amplification on the gel the PCR mix (generally consisting of enzymes, primers, nucleotides and so on) is arranged on top of the gel. The PCR mix is herein in contact only on the boundary surface with for instance, the acrylamides of the gel. In the case of amplification in the gel the PCR mix is situated in the gel. The PCR mix is now in full contact with the acrylamides.

Because there is no or hardly any difference in the size of the nucleic acid fragments with a mutation and the nucleic acid fragments without mutation, the different fragments according to the invention are separated from each other on the basis of differences in binding energy. The binding energy depends on the nucleic composition of the fragments. When a mutation is present in a nucleic acid fragment, for instance a substitution of a nucleotide, the binding energy will differ from the binding energy of the fragments without the mutation.

In order to separate the nucleic acid fragments with mutation from the nucleic acid fragments without mutation, a gradient resulting in at least partial melting of the double-stranded nucleic acid fragments, such as for instance an increasing temperature gradient, is applied. Because the double-stranded nucleic acid fragments with mutation have a binding energy differing from that of the double-stranded nucleic acid fragments without mutation, the fragments will become at least partially single-stranded (melt) at different temperatures. Owing to the at least partial melting the fragments are fixed at a specific location in the gel. Due to the difference in binding energy the double-stranded nucleic acid fragments without mutation will herein be fixed at a different position in the gel than the fragments with mutation. In this manner the nucleic acid fragments with mutation can thus be separated in the gel from the nucleic acid fragments without mutation (FIG. 1).

In order to ensure that the fragments are fixed at a specific location in the gel, the double-stranded fragments may not melt completely under the influence of the gradient resulting in at least partial melting. For this purpose a GC-rich tail ("GC clamp"; about 15 to 60 GC pairs) can for instance be added to one of the amplification primers. The GC clamp remains double-stranded in the gradient resulting in at least partial melting.

The mutually separated fragments can then be detected in the gel in conventional manner. Ethidium bromide, which binds to the nucleic acid fragments, is for instance added for this purpose to the samples before or during the electrophoresis step, whereby the fragments can be made visible using UV light. Other known methods of detection can however also be used according to the invention.

In a particularly suitable preferred embodiment of the method according to the invention, the method comprises the following step of:

(d) causing the double-stranded nucleic acid fragments present in the sample to melt completely into single-stranded nucleic acid fragments prior to step (b) and reforming double-stranded nucleic acid fragments from these single-stranded nucleic acid fragments, wherein heteroduplex double-stranded nucleic acid fragments are formed in addition to homoduplex double-stranded nucleic acid fragments.

Homoduplex double-stranded nucleic acid fragments (designated hereinbelow as homoduplex fragments) result when two "normal" (i.e. without mutation) single-stranded nucleic acid fragments or two mutated single-stranded nucleic acid fragments pair to form double-stranded nucleic acid fragments. Heteroduplex double-stranded nucleic acid fragments (designated hereinbelow as heteroduplex fragments) are formed when a normal single-stranded nucleic acid fragment pairs with a mutated single-stranded nucleic acid fragment (FIG. 2). Because both strands are then not exactly complementary, the heteroduplex fragments have a lower binding energy than the homoduplex fragments.

Complete melting of the double-stranded nucleic acid fragments into single-stranded fragments and reforming of double-stranded nucleic acid fragments from these single-stranded fragments can for instance be achieved by heating the sample, whereby the double-stranded fragments melt, and by then cooling the sample again, whereby the single-stranded fragments once again form double-stranded nucleic acid fragments, which are then separated from each other using gel electrophoresis.

As described above, the different nucleic acid fragments are then mutually separated on the basis of the differences in their binding energy in a gradient resulting in partial melting of the fragments. The heteroduplex fragments herein have a lower binding energy than the homoduplex fragments and will therefore partially melt and be fixed in the gel sooner.

When a heterozygotic mutation is present, four different double-stranded nucleic acid fragments will be formed, two homoduplex fragments and two heteroduplex fragments, as shown in FIG. 2. Heteroduplex fragments are characterized by the fact that at least one base does not pair, i.e. cannot bind with the opposite base. The two heteroduplex fragments have a lower binding energy and will therefore partially melt sooner than the homoduplex fragments and be fixed at a different specific location in the gel. Because the base pairs influence the binding energy of adjacent base pairs (immediately adjacent base pairs more, further removed pairs less) two different heteroduplex fragments will have a different binding energy. Due to the relative differences in the binding energy of the two heteroduplex fragments, these melt at different locations in the gel (i.e. for instance at a different temperature) and are thus fixed at different locations. In this manner different alleles can for instance be separated from each other.

The electrophoresis performed in the method according to the invention is preferably capillary electrophoresis. This technique is based on arranging the gel, for instance polyacrylamide, in a capillary. The sample is arranged in the capillary and a voltage is then applied over the capillary. The molecules present in the sample will migrate through the gel in the capillary at different speeds, depending inter alia on their size and/or charge, and are thus separated from each other. The advantages of capillary electrophoresis lie in the fact that the molecules, in this case the nucleic acid fragments, can migrate more rapidly in the capillary because a higher voltage can be applied over the gel in the capillary. The electrophoresis step can therefore be performed in a much shorter time. This is the result of the fact that a capillary is very chin, whereby the resistance of the gel in the capillary is high. When there is a high voltage over the gel the electric current, and therefore the generation of heat, hereby remains low. The ratio of surface area to volume of the capillary is moreover high, so that the generated heat can be discharged more readily and more quickly. A gel with a much lower viscosity (practically liquid) can also be arranged in a capillary. A much less dense and solid gel matrix can therefore be chosen. A further advantage is that very small samples can be analysed, which is particularly important when little material is available.

Owing to the very thin wall of the capillary and the high area:volume ratio, it will be further possible for the heat transfer to take place quickly and steep temperature gradients can be applied. A very rapid amplification step is hereby possible and the method according to the invention can thus be performed considerably faster.

In a further advantageous embodiment the method further comprises of:

(e) changing the electrophoresis conditions after step (b) such that the at least partially melted nucleic acid fragments once again become double-stranded, whereby the separated nucleic acid fragments migrate further from their specific location in the gel at a practically equal speed.

The separated nucleic acid fragments are herein preferably detected when they leave the capillary. By further electrophoresing the separated nucleic acid fragments the different fragments will leave the capillary in determined sequence. The fragments can here for instance be automatically detected by labelling the nucleic acid fragments before the separation with for instance a fluorescent label, and by exciting the fragments with a laser of the correct wavelength immediately before or as they leave the capillary. The fluorescence can then be detected using a photosensitive cell. For labelling of the DNA fragments use can be made of fluorescent substances, although other forms of labelling are also possible. By labelling the fragments the method becomes more sensitive and less material is required.

Other per se known forms of detection, for instance during the migration of the fragments in the capillary, are however also possible. It is for instance possible to expose the capillaries with UV light at different moments, wherein recordings can be made using a camera. In this manner the specific location of the fragments in the gel can for instance also be determined.

A particularly suitable preferred embodiment of the method according to the invention further comprises of isolating the separated nucleic acid fragments from the gel. The isolated fragments can subsequently be used for further analysis, such as for instance sequence determination.

The separated nucleic acid fragments can for instance be isolated when they leave the capillary. Another method of isolation consists of isolating the fragments from the gel after determining the specific location in the capillary (such as for instance using a camera as described above). For this purpose the (disposable) capillaries can for instance be cleaved at the correct position, whereafter the nucleic acid fragment can be isolated from the gel remnants in the piece of capillary. Separated alleles can for instance be sorted in this manner.

According to the invention the gradient resulting in at least partial melting of the double-stranded nucleic acid fragments is preferably a temperature gradient.

Through gradual or stepwise increase in the temperature it is possible to achieve in simple manner that the double-stranded nucleic acid fragments melt subject to their binding energy, and are thus fixed in the gel at their specific location. The temperature gradient can for instance be applied from the upper side of the capillary to the underside thereof, but can for instance also be a temperature gradient applied in time, i.e. from the beginning to the end of the experiment.

In another particularly suitable embodiment of the method according to the invention the gradient resulting in at least partial melting is a chemical gradient.

The chemical gradient is herein preferably formed by urea and formamide. In an increasing concentration of urea and formamide nucleic acid fragments will melt and be fixed in the gel more quickly as the fragments have a lower binding energy.

In addition to the aforementioned gradients, other gradients resulting in melting of the double-stranded fragments can also be applied according to the invention. Another preferred embodiment of the method is obtained when the gradient resulting in partial melting consists of a combination of a temperature gradient and a chemical gradient.

In a particular preferred embodiment of the method according to the invention, once the nucleic acid fragments have been mutually separated and fixed at their specific location in the gel, the electrophoresis conditions are changed as described above such that the partially melted nucleic acid fragments once again become double-stranded, whereby the separated fragments migrate further at the same speed from their specific location in the capillary. Changing the electrophoresis conditions herein preferably consists of reducing the temperature. By reducing the temperature in the capillary the partially melted fragments will become double-stranded again and will migrate further from their specific location in the gel at practically the same relative speed and leave the capillary in a determined sequence. Their relative speed is the same because the size of the double-stranded nucleic acid fragments with mutation does not differ, or hardly so, from the size of the nucleic acid fragments without mutation.

When the separation of the nucleic acid fragments in the gel has been effected by applying a chemical or other gradient, the temperature can be reduced in the same manner after the separation to make the at least partially melted fragments become double-stranded again.

The sample in which it is desired to detect one or more mutation(s) in the nucleic acid can consist of any suitable material from an individual in which genetic material is present in the form of nucleic acid, such as DNA and/or RNA, for instance blood, sperm, saliva and/or diverse tissue cells. The sample can first be processed in order to isolate the nucleic acid. Extraction and purification of the nucleic acid take place according to standard protocols which are known to the skilled person. When the nucleic acid present in the sample consists of single-stranded fragments, as for instance in the case of RNA, double-stranded nucleic acid fragments will first have to be made using known techniques. In the case of RNA use can for instance be made for this purpose of per se known PT-PCR techniques.

In the present application the term "mutation" relates to any change in a nucleic acid fragment relative to the "normal" (wild type) genetic material. The nucleotide sequence of the mutated nucleic acid herein displays one or more differences from the nucleotide sequence of the corresponding, non-mutated nucleic acid. Such a mutation can for instance be a point mutation (wherein a single base pair is generally different and is usually replaced by another base pair) or an insertion or deletion of one or more nucleotides. According to the present invention the term mutation further also relates to so-called polymorphisms, i.e. differences in the alleles occurring in the natural population for one determined gene.

The invention further relates to and provides a device with which the above described method can be performed.

The device according to the invention comprises a number of capillaries in which a gel is arranged, wherein both the upper side and the underside of the gel in the capillaries are in contact with a liquid bath in which an electrode is arranged, a voltage source for applying a voltage over the gel, means for changing the electrophoresis conditions during electrophoresis and means for detecting the separated DNA fragments.

Using the device the method according to the invention can be performed in simple and very rapid manner.

In a favourable embodiment of the device according to the invention the device comprises a large number of capillaries, wherein the upper side of the gel in the capillaries is in contact with one collective liquid bath for substantially all capillaries, wherein an electrode is arranged in the collective liquid bath, and the underside of each gel in the capillaries is in contact with separate liquid baths, wherein an electrode is arranged in each separate liquid bath.

By means of a suitable built-in voltage source a voltage can be applied between the electrodes over the gel in the capillary. The voltage applied over the gel can but does not have to be variable.

Detection means which can be used in the device according to the invention are for instance conventional detection means which are commonly used in for instance chromatography, such as for instance UV/visible light spectrophotometers. Fluorescence detecting means are preferably used since these are more sensitive. The nucleic acid fragments in the samples must however first be labelled for this purpose.

According to the invention the means for changing the electrophoresis conditions in the capillaries preferably consist of means for changing the temperature in the capillaries during electrophoresis.

In the device according to the present invention the means for changing the temperature preferably comprise a so-called Peltier element in which the capillaries are clamped, or a Peltier coil wound round the capillaries. A Peltier element consists of a strip from two different types of metal. By varying the strength and/or direction of the current through this element the element can both cool and heat (the so-called Peltier effect). Other means with which the temperature in the capillary can be changed during electrophoresis are possible, such as heating means which heat the area surrounding the capillary, such as for instance a (halogen) lamp, and cooling means which for instance blow cold air along the capillary to reduce the temperature in the capillary, such as for instance a fan.

Because the underside of each gel in the capillaries is in contact with separate liquid baths, the separated nucleic acid fragments can be isolated in simple manner by exchanging the liquid baths after a specific fragment has left the capillary. The liquid baths contain normal, per se known electrophoresis buffers from which the isolated nucleic acid fragments can then be recovered using per se known techniques such as precipitation or concentration, and used for further analysis.

In a particularly suitable preferred embodiment of the device means for measuring the temperature are arranged in at least one capillary. During the amplification step the temperature in the capillaries must be regulated quickly and as precisely as possible. By arranging the means for measuring the temperature in a capillary a very reliable indication is obtained of the temperature prevailing in the capillaries during the amplification step.

The means for measuring the temperature can herein be embodied in any manner suitable for this purpose. The means for measuring the temperature preferably comprise a platinum resistance wire arranged in at least one capillary. The capillary can herein be filled with for instance water and sealed, so that a capillary is obtained having practically the same heat capacity as the other capillaries.

In a further particular preferred embodiment of the device the capillaries are coated with primers and dNTPs for amplifying in the capillary, in or on the gel, the nucleic acid fragments present in the sample. In this manner only those samples in which the mutation is to be detected and the polymerase have to be loaded onto the capillary. More preferably the capillaries are coated with primers, dNTPs and polymerase.

The invention also relates to and provides the capillaries for use in the method and device as described above, wherein the capillaries are coated with primers and dNTPs and more preferably with primers, dNTPs and polymerase. Use can for instance be made for this purpose of disposable capillaries coated on the inner side.

BRIEF DESCRIPTION OF THE DRAWINGS

The invention will be further illustrated with reference to the annexed figures, in which.

DETAILED DESCRIPTION OF THE INVENTION

Figure 1:
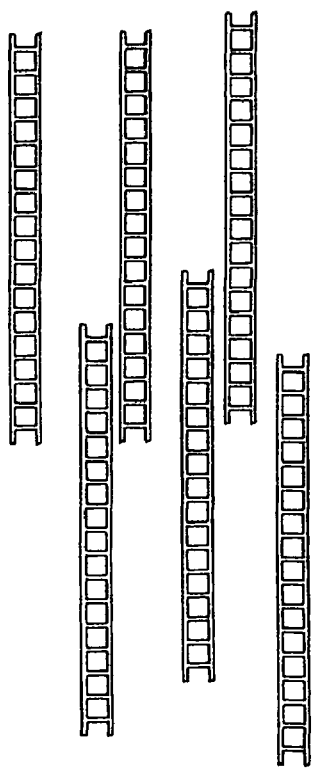
FIG. 1 shows a schematic representation of the partially melted DNA fragments (step b of the method according to the invention)
Figure 1:
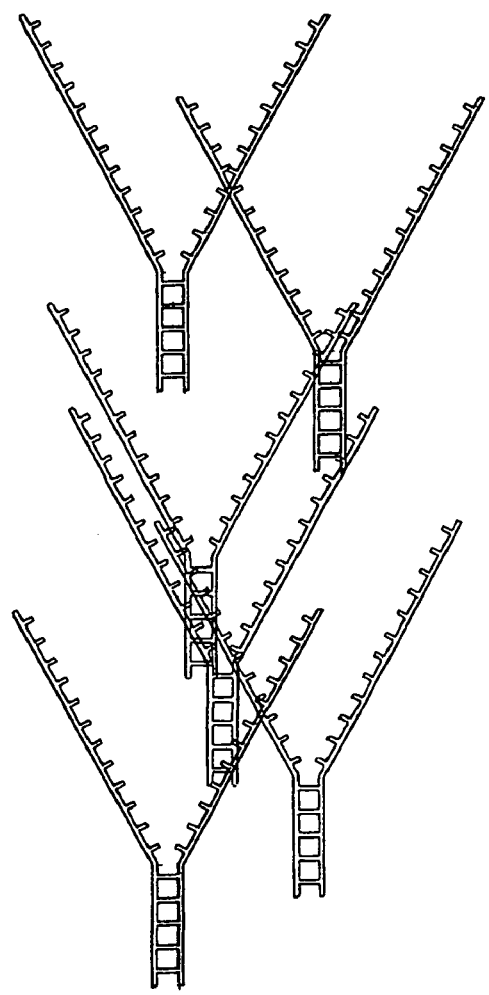
Figure 2:
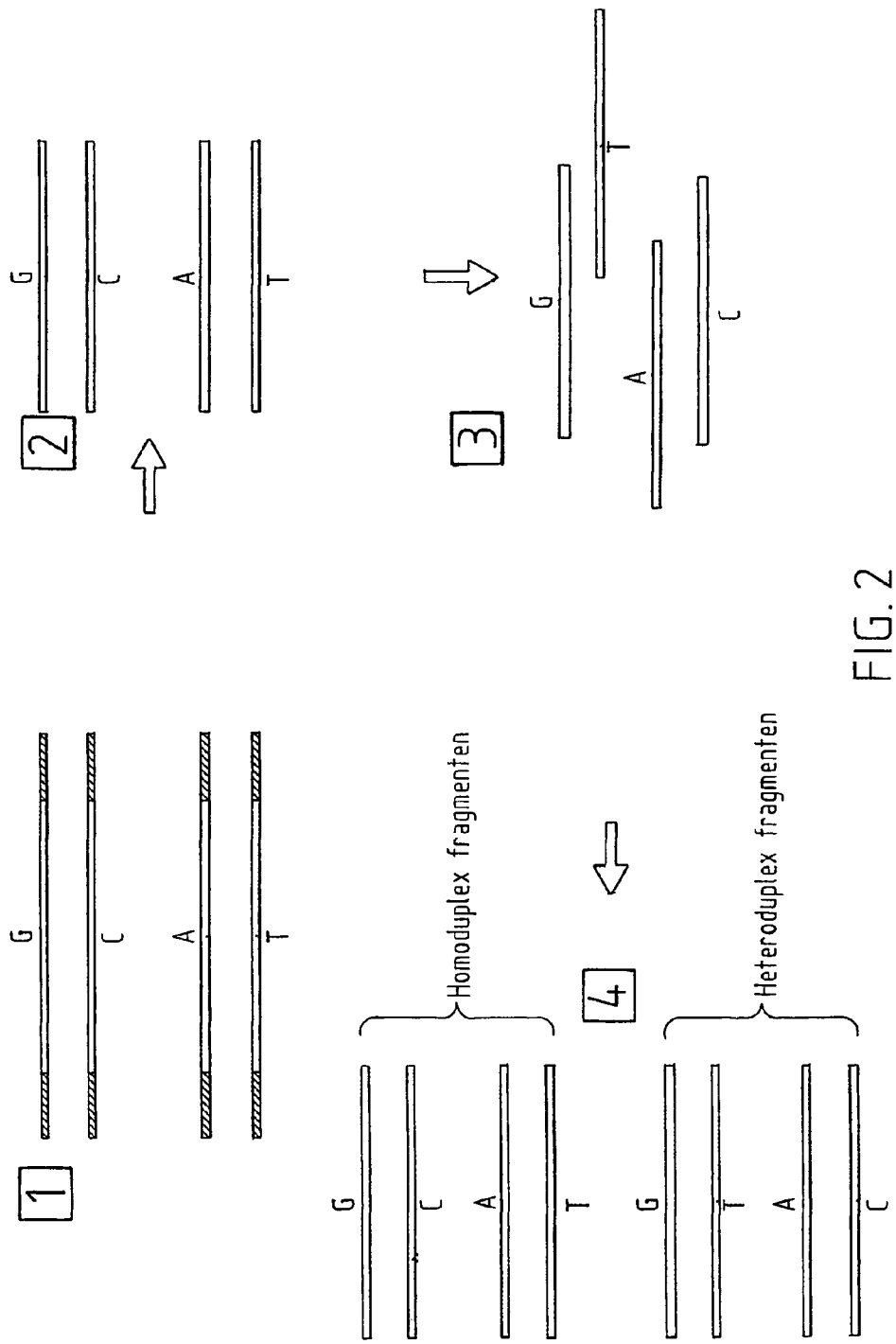
FIG. 2 shows schematically the forming of homo- and heteroduplexes (step d in the method according to the invention)
Figure 3:
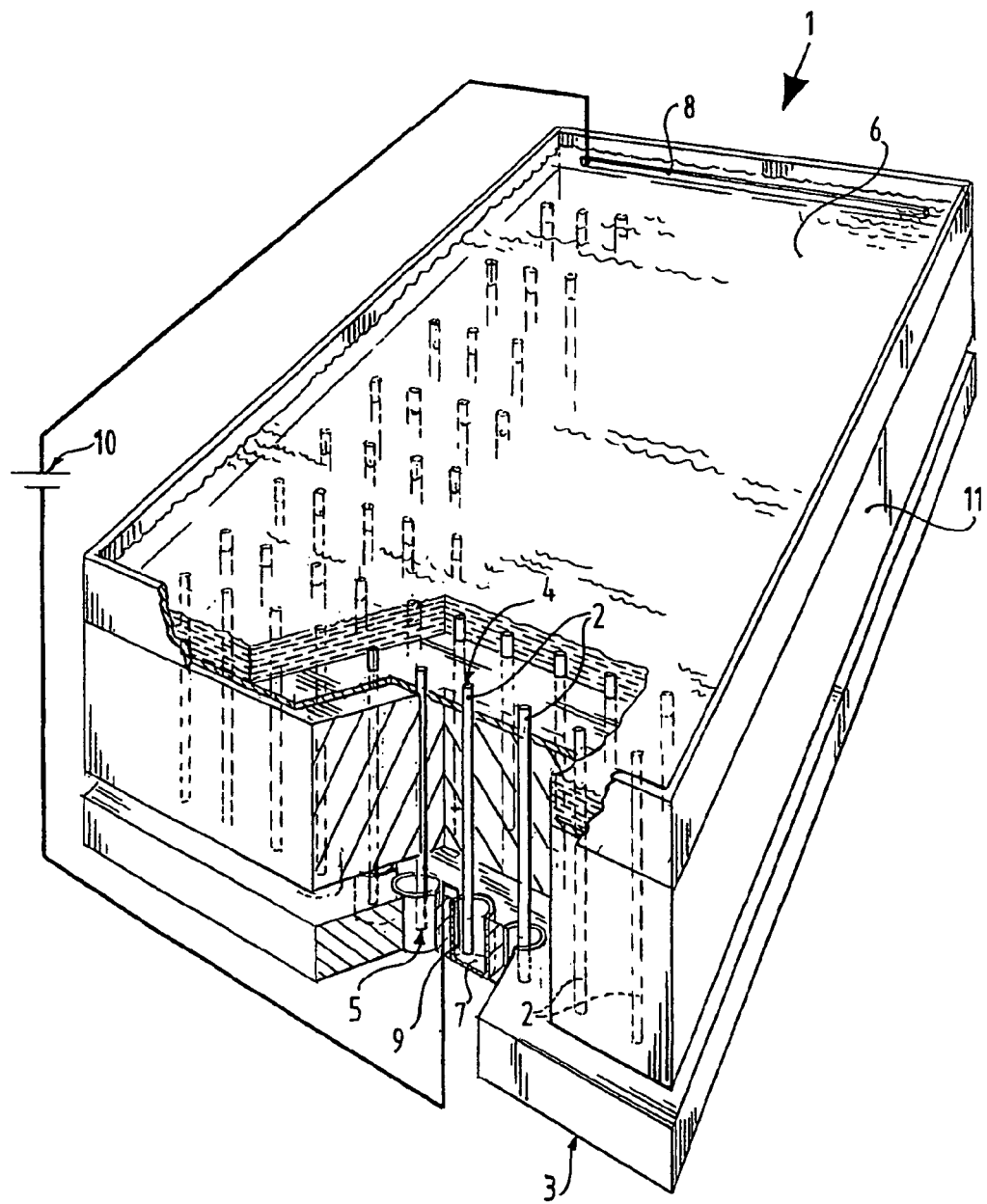
FIG. 3 shows a schematic view (partly in cross-section) of a preferred embodiment of the device according to the present invention.

As shown in FIG. 3, device 1 comprises a large number of capillaries 2 in a container 3, wherein a gel is arranged in the capillaries. Both the top side 4 and the bottom side 5 of the gel in capillaries 2 are in contact with a liquid bath 6,7 in which respectively a cathode 8 and an anode 9 are arranged. The upper side 4 of the gel in capillaries 2 is in contact with one collective liquid bath 6 for the capillaries with cathode 8 therein, and the underside 5 of the gel in each capillary 2 is in contact with separate liquid baths 7, wherein an anode 9 is arranged in each separate liquid bath 7. This is shown in more detail in FIG. 4. Device 1 further comprises a voltage source 10, as well as means for changing the temperature 11 consisting of a so-called Peltier block in which the capillaries are fixedly clamped, as also shown schematically in FIG. 4.

Figure 4:
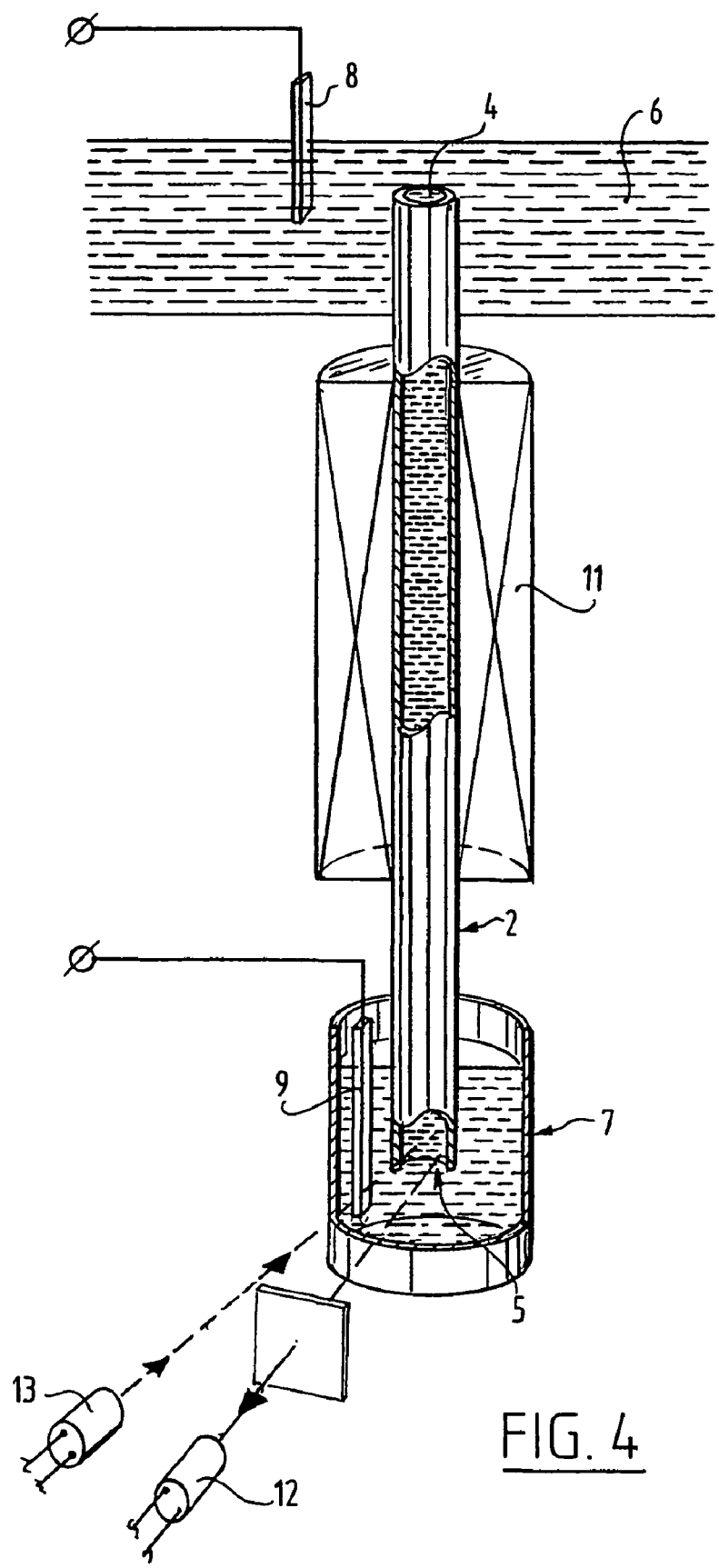
FIG. 4 shows a detail of FIG. 3.

In the preferred embodiment shown in FIG. 4 means 12 are further present for detecting the separated nucleic acid fragments, which means detect the nucleic acid fragments as they leave capillary 2. The detection means comprise for instance a diode laser 13 which excites the labelled nucleic acid fragments and wherein the fluorescence emitted by the fragments is detected by a fluorescence detector 12.

Figure 5:
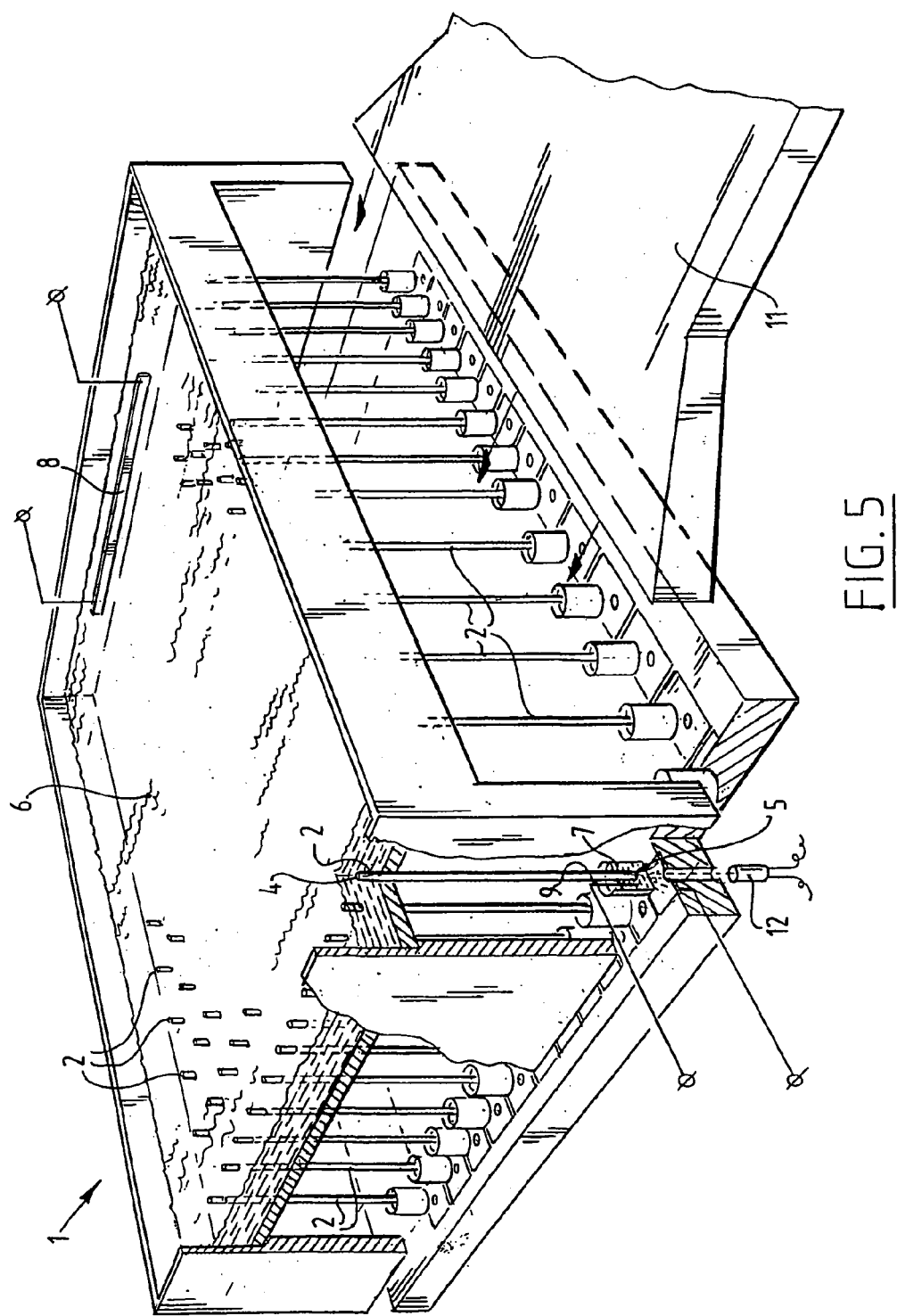
FIG. 5 is a schematic view, partly in cross-section, of another suitable preferred embodiment of the device according to the invention.

FIG. 5 shows another advantageous embodiment of the device according to the invention. Device 1 herein likewise comprises a number of capillaries 2 in which a gel is arranged; the upper side 4 of which is in contact with one collective liquid bath 6 for all capillaries and in which the cathode 8 is arranged, and the undersides 5 of which are in contact with separate liquid baths 7 in which the separate anodes 9 are arranged. The means for changing the temperature 11 are formed in this embodiment by heating means which increase the temperature in the capillaries (not shown), and cooling means which blow cool air along the capillaries.

As detection method in the method according to the invention use can be made of for instance UV exposure and a high resolution CCD camera. EtBr or SyBr-gold labelled fragments can for instance be detected herewith. Fragments with fluorescent labelling can for instance be detected using a colour CCD camera; use is made herein of a filter to block UV light. The different colours can be made visible afterward using software suitable for this purpose.

The invention claimed is:

1. A method for detecting one or more mutations or polymorphisms in a nucleic acid fragment in a sample, comprising the following steps, to be performed in suitable sequence, of:
   (a) amplifying the nucleic acid fragment present in the sample with polymerase chain reaction (PCR) occurring in or on a quantity of electrophoresis gel arranged within a capillary;
   (b) subsequently separating the nucleic acid fragments by applying a voltage over said capillary in the presence of a gradient resulting in at least partial melting of the nucleic acid fragments formed in step (a), for the purpose of fixing the partially melted nucleic acid fragments at a specific location in the electrophoresis gel; and
   (c) detecting separated nucleic acid fragments.

2. The method as claimed in claim 1, further comprising step (d) causing the double-stranded nucleic acid fragment present in the sample to melt completely into single-stranded nucleic acid fragments prior to step (b), and reforming a double-stranded fragment from the single-stranded nucleic acid fragments, wherein a heteroduplex double-stranded nucleic acid fragment is formed in addition to a homoduplex double-stranded nucleic acid fragment.

3. The method as claimed in claim 1, wherein the method further comprises step (e) changing electrophoresis conditions after step (b) such that the at least partially melted double-stranded nucleic acid fragment once again becomes double-stranded, wherein the separated nucleic acid fragments migrate further from their specific location in the electrophoresis gel at a practically equal speed.

4. The method as claimed in claim 1, wherein the separated nucleic acids are detected when they leave the capillary.

5. The method as claimed in claim 1, further comprising the step of isolating the separated nucleic acid fragments from the electrophoresis gel.

6. The method as claimed in claim 1, wherein the gradient in the electrophoresis gel that partially melts the double-stranded nucleic acid fragment is a temperature gradient.

7. The method as claimed in claim 1, wherein the gradient that partially melts the double-stranded nucleic acid fragment is a chemical gradient.

8. The method as claimed in claim 7, wherein the chemical gradient is formed by urea and formamide.

9. The method as claimed in claim 6, wherein the gradient comprises a combination of a temperature gradient and a chemical gradient.

10. The method as claimed in claim 2, further comprising the step of:
    changing electrophoresis conditions such that the at least partially melted double-stranded nucleic acid fragment once again forms a double-stranded nucleic acid fragment by reducing temperature in the electrophoresis gel.

11. The method as claimed in claim 1, wherein the sample comprises genetic material from an individual wherein the genetic material is present in the form of nucleic acid selected from the group consisting essentially of: blood, sperm, saliva and tissue cells.

* * * * *